United States Patent [19]

Tiemann

[11] 4,180,791
[45] Dec. 25, 1979

[54] SIMPLIFIED SECTOR SCAN ULTRASONIC IMAGING SYSTEM

[75] Inventor: Jerome J. Tiemann, Schenectady, N.Y.

[73] Assignee: General Electric Company, Schenectady, N.Y.

[21] Appl. No.: 884,951

[22] Filed: Mar. 9, 1978

[51] Int. Cl.² ............... G01S 9/66; G01S 9/68; G01N 29/00
[52] U.S. Cl. ...................... 367/105; 73/626; 367/7
[58] Field of Search ............... 340/1 R; 73/625, 626, 73/628

[56] References Cited

U.S. PATENT DOCUMENTS

| 2,549,872 | 4/1951 | Willard | 340/8 L |
| 4,012,952 | 3/1977 | Dory | 73/626 |
| 4,058,003 | 11/1977 | Macovski | 73/626 |

Primary Examiner—Richard A. Farley
Attorney, Agent, or Firm—Donald R. Campbell; Joseph T. Cohen; Marvin Snyder

[57] ABSTRACT

A curved transducer array or a flat array with an acoustic converging lens functions as a fixed focus physical lens and is focused near maximum range. At longer ranges the full aperture is utilized for good resolution, and at shorter ranges up to a specified fraction of maximum range improved resolution is achieved by a dynamic aperture control which increases the array aperture by steps by switching in more transducer elements. This simplified sector scanner does not require dynamic electronic focusing.

12 Claims, 5 Drawing Figures

SIMPLIFIED SECTOR SCAN ULTRASONIC IMAGING SYSTEM

BACKGROUND OF THE INVENTION

This invention relates to ultrasonic imaging systems, and more particularly to a simplified sector scanner with a fixed focus transducer array assembly in combination with a dynamic aperture control for acceptable resolution at both shorter and longer ranges.

The single-sector scanner is a real time imaging system in which the elementary transducers of a linear array are excited in time sequence to generate angulated acoustic beams at many angles relative to the normal to the array at its midpoint. Echoes returning from targets in the direction of the transmitted beam arrive at the array elements at different times necessitating relative delaying of the received echo electrical signals by different amounts so that all the signals from a given point target are summed simultaneously by all elements of the array. In addition to beam steering delays, dynamic electronic focusing to improve image quality is achieved by additional channel-to-channel delay differences to compensate for propagation path time delay differences from a focal point to the array element positions. A cardiac scanner with dynamic time delay focusing to increment the range from which echoes are being received during a reception period is described by Thurstone and von Ramm in "A New Ultrasonic Imaging Technique Employing Two-Dimensional Electronic Beam Steering", *Acoustical Holography*, Vol. 5, 1974, Plenum Press, New York, pp. 249-259. In such prior art fixed aperture sector scanners, all the receive elements are active during every echo reception period and contribute to coherent summation to generate the focused echo signal. One problem with dynamic electronic focusing is that at short ranges less than the full aperture, dynamic focusing delays must be made so rapidly that it becomes impossible to keep up, and another problem is that such changes just before coherent summation have the potential of producing artifacts in the display.

A dynamic array aperture and electronic focus control for sector scanners and other imaging systems is disclosed and claimed in allowed copending commonly assigned application Ser. No. 864,597 filed on Dec. 27, 1977 by Charles E. Thomas. As the range from which echoes are being received propagates out, the array aperture during every echo reception period is increased by steps by switching in more transducer elements. At least one adjustment of focusing time delays is made to dynamically focus the echoes at different focal points. Improved lateral resolution is attained especially at ranges less than the full aperture by adjusting the aperture size incrementally.

The present invention is directed to a low cost single sector ultrasonic imager which does not require dynamic focusing. Conventional fixed focus, fixed aperture systems—with a physical lens achieved by curving the transducer array or by an acoustic lens in front of a flat array—focus the lens near the middle of the intended field of view. This produces degraded resolution at both the near and far extremes of the field of view, and to minimize this problem a relatively small aperture must be chosen. Consequently, the resolution is rather limited.

SUMMARY OF THE INVENTION

A simplified sector scanner ultrasonic imaging system has a fixed focus physical lens which is focused near maximum range such that with a properly selected full array aperture there is acceptable resolution in the region between a specified fraction of maximum range (such as about 0.5) and maximum range. A dynamic aperture control is effective to reduce the aperture in regions closer to the transducer array, and the fixed focus, dynamic aperture system has good or acceptable resolution at both longer and shorter ranges.

The fixed focus physical lens is a curved transducer array but can also be a flat array with a converging acoustic lens; in either case the row of transducer elements are at physical locations such that there are equal time delays for sound propagating from the focus to all elements of the array. The focal length of the physical lens is desirably equal to 0.8 to 0.9 times the maximum range. The dynamic aperture control is operative to increase the number of active array elements and receiving channels as a function of range during every echo reception period to thereby increase the array aperture by steps between minimum range and the specified fraction of maximum range, the full aperture being maintained thereafter out to maximum range. The full aperture and reduced aperture at any step change are chosen so that a preselected time error is not exceeded for echoes received by active array elements and originating at coordinated ranges. The aperture control can be comprised of a gain control or switch in every receiving channel, one channel per array element, a range computer in the form of a counter which is cleared at the beginning of each transmit-receive cycle, and a controller responsive to the counter output for initially closing a central group of switches and then closing other pairs of switches, one at either side, to increase the array aperture symmetrically by steps.

DESCRIPTION OF THE PREFERRED EMBODIMENT

A curved transducer array for making sector scans, or an equivalent flat linear transducer array with a converging acoustic lens, functions as a fixed focus physical lens and is focused near maximum range. Provided that the array aperture is properly chosen so that a predetermined time error is not exceeded, the full aperture is employed for good lateral resolution at ranges greater than a specified fraction of maximum range. The problem of generally poor image quality in regions close to the transducer array under these conditions, when a transducer of relatively wide aperture is focused at a point near the maximum range at which it is to be used, is overcome with little additional complexity by reducing the array aperture when echoes from nearby scatterers are being received. Lateral resolution refers to the minimum separation at which two targets can be distinguished in the direction of the longitudinal axis of the linear transducer array, and under near-field conditions lateral resolution improves as the array aperture decreases. A class of low cost ultrasonic imaging systems is described which do not require any dynamic electronic focusing, but which provide considerable improvement over conventional fixed focus, fixed aperture systems.

Figure 1:
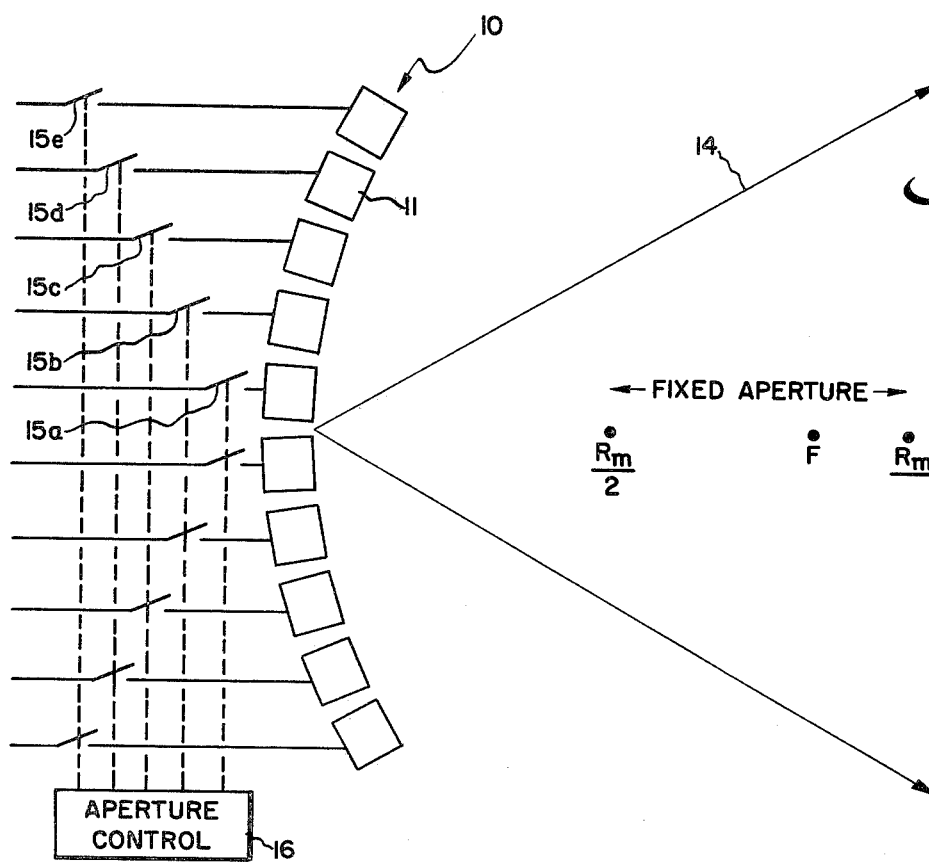
FIG. 1 shows a curved transducer array with a fixed focus F and aperture control switches for dynamically changing the array aperture.
Figure 2:
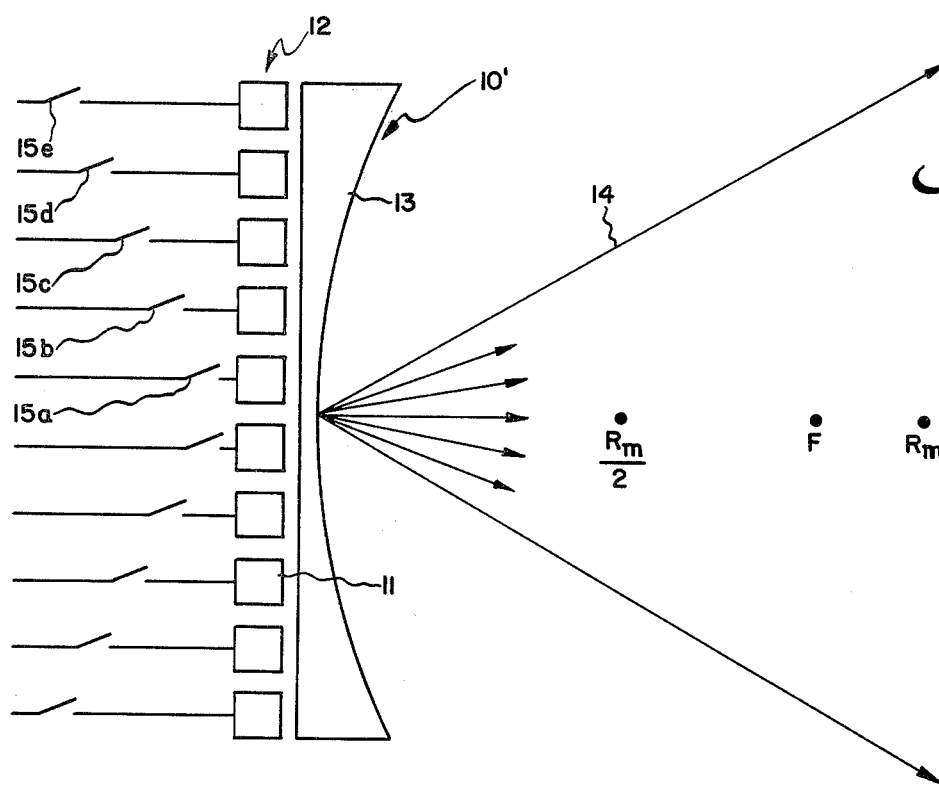
FIG. 2 is similar to FIG. 1 except that a flat transducer array and converging acoustic lens are substituted for the curved array.

In FIG. 1, transducer array assembly 10 is a curved array comprised of a single row of elementary transducers 11 which are equally spaced in the direction of the longitudinal axis of the array. The physical locations of the array elements along the curve are such that there are equal time delays for sound propagating from a focus F to all elements of the array. The curved transducer array may also be referred to as a fixed focus physical lens. Transducer elements 11 are typically made of piezoelectric materials and can also be curved in the transverse direction, perpendicular to the plane of the paper, in which case the array can be said to be shaped like a section of the wall of an inner tube. An alternative embodiment of the fixed focus physical lens is illustrated in FIG. 2. Transducer array assembly 10' comprised of a flat transducer array 12 having a single row of elementary transducers 11 with which is combined a converging acoustic lens 13. The acoustic lens is mounted in front of the transducer array and is made of a material, such as an appropriate plastic, in which the velocity of sound is faster than in water or tissue. As with the curved array, there are isochronous path delays for sound between focus F and all elements of the array.

The focal length of the physical lens or transducer array assembly is chosen such that the time error at the extremes of the array as compared to the center element has the same magnitude for a sound source at the maximum range, $R_m$, as for a sound source at a range equal to some specified fraction of the maximum range. When the specified fraction is equal to 0.5, that is, if the time error is constrained to be the same at $R_m/2$ as it is at $R_m$, it can be shown that the focal length is chosen to be $$f = 0.828 \, R_m.$$

Provided that the full array aperture is properly selected as will be explained later, acceptable resolution is realized for echoes generated at ranges between $R_m/2$ and $R_m$ with a fixed aperture. The full aperture is employed at these longer ranges since under far field conditions lateral resolution improves as the transducer array aperture increases. The time error criterion places a constraint on the maximum aperture for the system and the resolution is not as high as for systems with larger apertures, but there is useful resolution for many medical and industrial imaging applications. The specified fraction of maximum range, given as 0.5 for the preferred embodiment, can have other values but is preferably chosen so that the focus F is at a range equal to 0.8 to 0.9 times the maximum range, $R_m$. The focal length of the physical lens is calculated from well-known equations.

Dynamic aperture control is needed at ranges closer to the array assembly than the specified fraction, given as $R_m/2$ in the example, in order to obtain improved lateral resolution at shorter ranges. As the region from which echoes are being received propagates out, the array aperture is increased by steps by switching in more elements of the total transducer array. The number of active array elements and receiving channels contributing to coherent summation and generation of a focused echo signal increases as a function of range up to the specified fraction of maximum range, and thereafter out to maximum range all the array elements and receiving channels are active and make contributions to coherent summation. The dynamic aperture control changes the size of the array aperture at shorter ranges during every echo reception period, following generation of an angulated acoustic beam by pulsing the elements in time sequence. By progressively changing the time delay between successive excitation pulses, the angle at which the pulse of ultrasound is transmitted is changed by increments. The total sector scan angle is approximately 60 to 90 degrees and several acoustic scan lines 14 originating at the midpoint of the array are depicted in FIGS. 1 and 2. Echoes returning from targets in the direction of a transmitted beam arrive at the transducer elements at different times necessitating relative delaying of the received echo electrical signals by different amounts so that all the signals from a given point target are summed simultaneously by all elements of the array. The magnitudes of the time delays of the individual echo electrical signals are the same as during the transmission operation, and are referred to as the beam steering time delays or simply steering delays. An implementation of the receiver with provision in the individual receiving channels for amplifying and delaying the echo signals, and summing the delayed signals from the varying number of active channels in an echo reception period, is given in FIG. 5.

Aperture control to improve lateral resolution at shorter ranges is implemented by structuring the receiver so that the individual channels can be blanked electronically with the possible exception of a central group of receiving channels. The dynamic aperture control is shown schematically in FIG. 1 as pairs of receiver channel switches 15a–15e which are closed in sequence during the echo reception period, one pair at a time, by an aperture control circuit 16. These switches operate at high speed and are actually electronic switches, but the function of blanking the channels can be performed in an equivalent manner as by reducing the amplifier gain. At the minimum range, only the two central array transducers are active and the delayed echo signals in only these two channels are summed to generate the focused echo signals. As the range increases, the two switches 15b on either side are closed and then pairs of switches 15c–15e are closed in sequence, thereby incrementally increasing the size of the receiver sub-array and the number of active receiving channels whose delayed echo signals are summed. Two or more adjacent pairs of switches can be closed simultaneously to obtain the desired aperture size. As a rule of thumb in the near field, beam width is approximately equal to the size of the aperture and lateral resolution varies with aperture size and is best when the aperture is small. At the specified fraction of maximum range, for example $R_m/2$, all the array elements and receiving channels are active and the full aperture is maintained out to the longest range.

Figure 3:
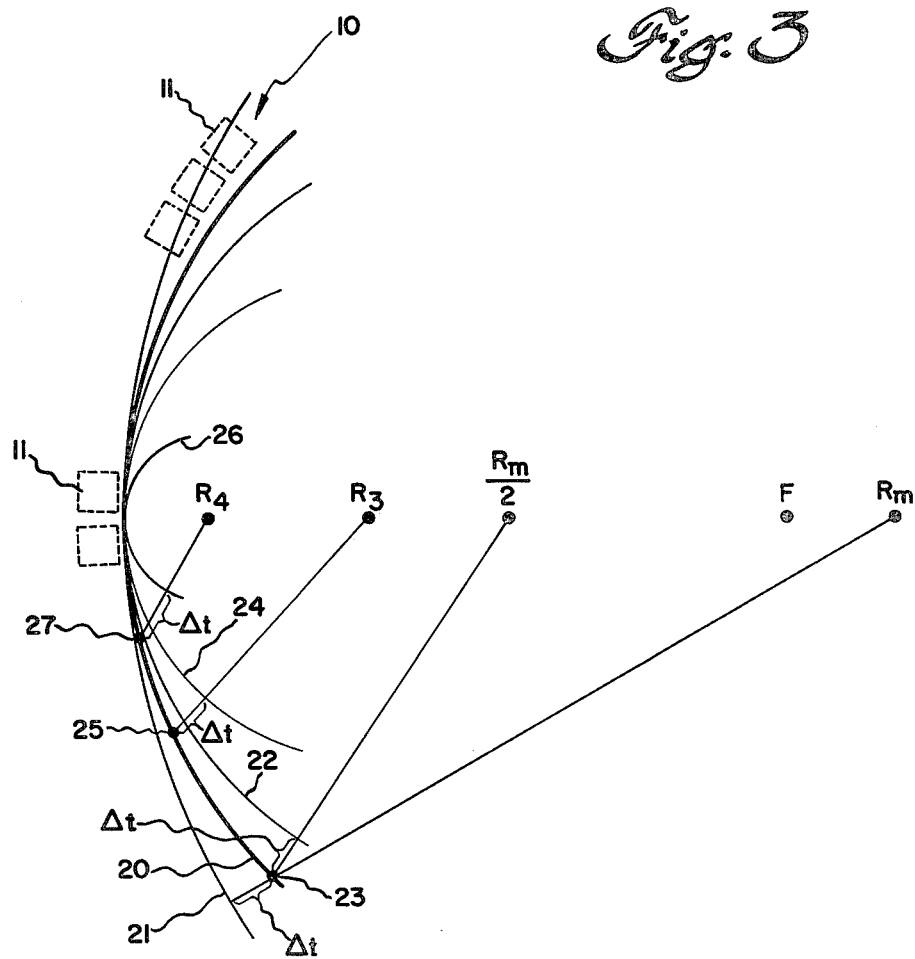
FIG. 3 is a sketch for explaining the time error criterion determining the curvature of the curved transducer array and allowable apertures at different ranges.

FIG. 3 facilitates explanation of the time error criterion determining the curvature of curved transducer array 10 as well as the permissible aperture at different ranges such that the error criterion is not exceeded and the resolution at all ranges is reasonable. Heavy curve 20 is placed at the face of the curved transducer array and physical locations of several array elements 11 are shown in dashed lines. Light circles 21 and 22 respectively have centers at $R_m$ and $R_m/2$, and both circles pass through the midpoint of the curved transducer array. Acoustic energy originating at $R_m$ has equal propagation path time delays to any point on circle 21, and there are equal time delays from $R_m/2$ to any point on circle 22. The focal length of the fixed focus physical lens is chosen such that the time error at the ends of the array have the same magnitude for a sound source at $R_m$ as for a sound source at $R_m/2$. Assume that the time error criterion is 1/6 of a period of the transducer frequency, which is the same as 1/6 of a wavelength of ultrasound at the frequency being employed. This error is reasonable because a vector at a 60° angle has a projection on the resultant substantially in excess of 0.5. Designating the 1/6 of a period time error as $\Delta t$, point 23 on curve 20 is the widest half aperture distance at which the error $\Delta t$ for echoes from $R_m$ and the error $\Delta t$ for echoes from $R_m/2$, positive in one case and negative in the other, do not exceed the allowable error. A larger half aperture, it is noted, is not permissible because lateral resolution degrades as the time error exceeds 1/6 of a period by larger and larger amounts. The maximum aperture, $W_{max}$, of the array can be shown to be:

$$W_{max} = 2.53\sqrt{R_m V/F_{res}},$$

where V is the velocity of sound, and $F_{res}$ is the resonant frequency of a transducer element. The resolution at $R = R_m$ is:
TI $X = 0.593\sqrt{R_m V/F_{res}} = 0.234\ W_{max}$.

The half aperture size such that a chosen time error criterion is not exceeded at that point is illustrated in FIG. 3 for echoes generated at ranges $R_3$ and $R_4$, both less than $R_m/2$. Circle 24 is the position of circular wave fronts radiating from $R_3$, and the general approach is to compute the aperture at which this circle differs from curve 20, measured along a radial line passing through $R_3$, by a given $\Delta t$ criterion at that point. Point 25 along curve 20 is the half aperture size at which the $\Delta t$ criterion is not exceeded, and this aperture is chosen to receive echoes emanating from targets at range $R_3$. Circle 26 having its center at $R_4$ has an even smaller radius and the given $\Delta t$ criterion, as measured by the distance between circles 26 and 20 along a radial line, is exceeded at a relatively small half aperture. Point 27 along curve 20 is the proper half aperture size for echoes emanating from range $R_4$.

Figure 4:
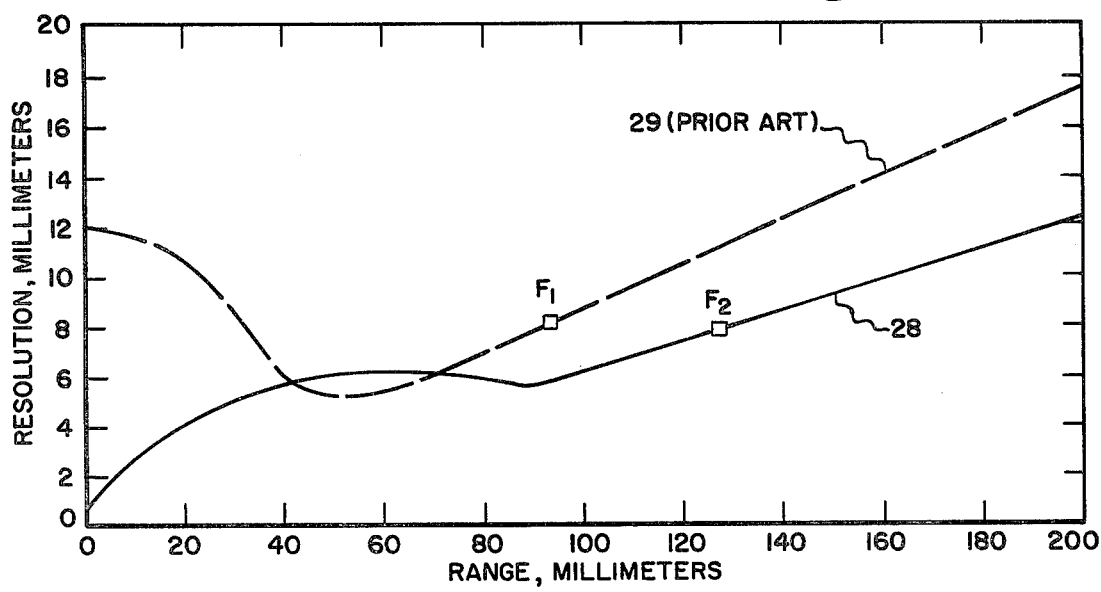
FIG. 4 are curves of resolution vs. range for a prior art fixed focus, fixed aperture system and the present fixed focus, variable aperture system.

FIG. 4 is a plot of resolution versus range for the present fixed focus physical lens, dynamic electronically controlled aperture system (curve 28) as compared to the conventional prior art fixed focus physical lens, fixed aperture system (curve 29). The focal point $F_1$ of the prior art system physical lens is somewhere near the middle of the intended field of view, whereas the focal point $F_2$ of the physical lens for the instant fixed focus, dynamic aperture system with a 50 percent larger maximum aperture is at a substantially greater range. As compared to the prior art system, the instant system has an improved focus and lateral resolution in both the short range and long range regions. At very short ranges, there is marked improvement as the aperture is increased as a function of range, rather than being fixed. In the relatively narrow region where the resolution of the prior art system is better, the difference in resolution is not great.

Figure 5:
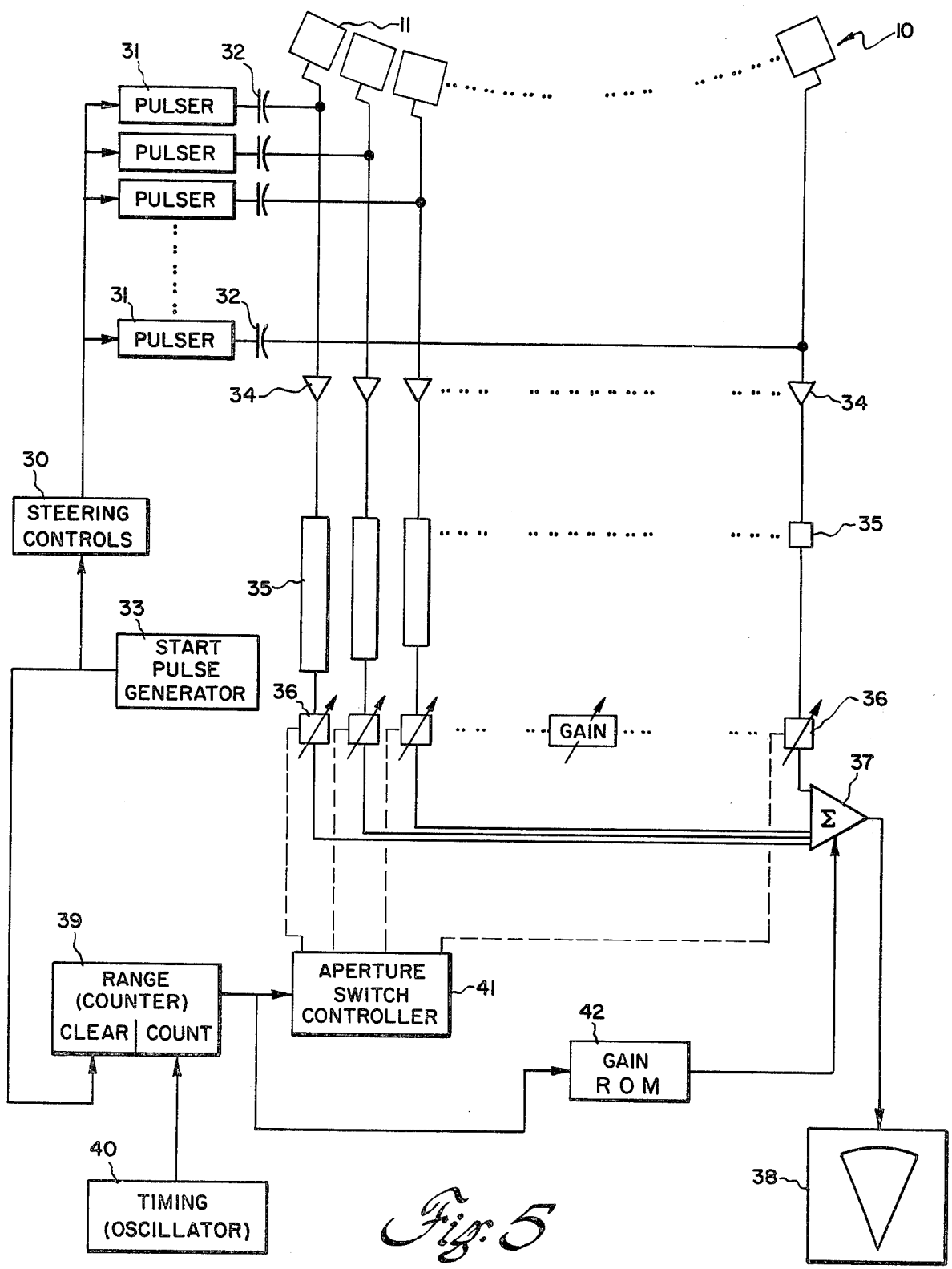
FIG. 5 is a system block diagram of a simplified single sector scanner imaging system incorporating a fixed focus physical lens in combination with a dynamic aperture control at shorter ranges.

FIG. 5 is a system block diagram of a simplified single sector scanner ultrasonic imaging system as constructed according to a preferred embodiment of the invention. The transducer elements 11 of curved transducer array 10 are connected to a like number of transmitting channels having the capability of producing element excitation pulses in time sequence to steer the generated angulated acoustic beams. Steering controls 30 contain adjustable delays and trigger transmit pulsers 31 in sequence to generate excitation pulses which are applied through capacitors 32 to the array elements. A start pulse generator 33 produces a series of pulses for controlling generation of the acoustic beams and operation of the imager as the sector scan is made. The parallel receiving channels for every array element 11 each include a preamplifier 34 having a limiter to protect the sensitive preamplifier inputs from the high transmitting voltage, an adjustable delay element 35 such as a charge coupled device (CCD) delay line for time delaying the received echo electrical signal to focus the echoes, and a receiver channel gain control 36 which is initially set to a low value and can be turned up at a selected time to selectively blank the individual channels during the intial part of the echo reception period. The steering delays are depicted as rectangular blocks which vary in length from channel to channel and have a magnitude determined by the steering control. The delayed echo signals from the changing number of active receiving channels are fed to a summing amplifier 37 to effect coherent summation, and the output is a focused echo signal or raw video data which may be post processed to improve the picture quality before being fed to a cathode ray tube 38 or television monitor for visual display in real time.

The dynamic aperture control includes, in addition to receiver channel gain control mechanisms 36, a range computer such as a counter 39 for calculating the echo propagation distance during every reception period. Counter 39 continuously counts up in response to a train of equally spaced pulses from a timing oscillator 40, and is cleared by the start pulse from generator 33 at the beginning of every transmit-receive cycle. The velocity of sound in tissue is about 154,000 centimeter per second and the range from which echoes are being received is known from the elapsed time for wave propagation of sound. The counter output thus changes as the range increases and controls operation of an aperture switch controller 41, which can be a read-only memory with an address section. As the count increments, higher addresses are accessed and the bits of a word read out of read-only memory controls the individual receiver channel gain contols 36. The array aperture is increased by steps as a function of range by initially setting to a high value the gain controls of a central group of channels and thereafter selecting the high gain value for other pairs of channels, one at either side, until the full aperture is opened up at the specified fraction of maximum range and maintained thereafter out to maximum range or even beyond. The number of channels set to active condition as the array aperture is symmetrically increased by increments depends upon the precalculated aperture at a given range such that a chosen time error criterion is not exceeded. This was clearly reviewed in the description of FIG. 3.

At shorter ranges when the array aperture is being increased and the number of active receive elements and receiving channels contributing to coherent summation during the echo reception period is changing rapidly, the quality of the video image is improved by compensating the overall gain of the focused echo signal. It is desirable to include in the system a gain read-only memory 42 that is operative to adjust the gain of summing amplifier 37 so that, as the aperture changes, the magnitude of the focused signal is the same after the change as before the change. There are then no lines across the screen of the cathode ray tube 38 at ranges where there is an expansion of array aperture. The compensation of amplifier gain is coordinated with the advancing range, and the count at the output of counter 39 also functions to address gain ROM 42. Although the array aperture and amplifier gain compensation are adjusted dynamically during the echo reception period, the steering delays provided by delay elements 35 remain the same and are changed only for a new transmit-receive cycle.

The components of a simplified ultrasonic scanner with a fixed focus physical lens and dynamic aperture control can be standard integrated circuits or conventional circuitry as is presently known in the art. Further information on sector scanners for real time imaging is given in the previously referenced publication and patent applications.

In conclusion, a low cost, ultrasonic imaging system has been described which does not require any dynamic focusing but which provides considerable improvement over conventional fixed focus systems. The simplified system has a physical lens for which a fixed focus is chosen somewhere near the maximum range. The full aperture is acceptable beyond a specific point, and the array aperture is expanded as a function of range in regions closer than that point. In this way good resolution is attained at both longer ranges and shorter ranges. This ultrasonic sector scanner has various applications in medical instrumentation for cardiology and laminography, where good images with reasonable lateral resolution in the near field region are needed, and in imaging equipment for industrial nondestructive testing applications. For cardiac scanning in real time a frame rate of about thirty frames per second is required, and the maximum range is about 25 centimeters. Good resolution and image quality over the entire field of view, from close to the transducer array all the way out to maximum range, are desirable.

While the invention has been particularly shown and described with reference to a preferred embodiment thereof, it will be understood by those skilled in the art that various changes in form and details may be made therein without departing from the spirit and scope of the invention.

The invention claimed is:

1. A sector scan ultrasonic imaging system comprising:
    a transducer array assembly including a row of transducer elements at physical locations such that there are equal time delays for sound propagating from a focus to all elements of the array, said array elements being selectively operable during alternate transmission and echo reception periods to generate angulated beams of ultrasound for scanning an object region and to generate received echo electrical signals,
    a plurality of transmitting channels for producing array element excitation pulses in time sequence, and a plurality of receiving channels for variably delaying the received echo signals to focus the echoes,
    aperture control means for increasing the number of active array elements and receiving channels as a function of range during each echo reception period such that a central group of receiving channels are initially active and thereafter pairs of receiving channels, one on either side, are additionally rendered active to change the array aperture by steps between the minimum range and a specified fraction of maximum range, the full aperture being maintained thereafter out to maximum range, and
    means for summing the delayed echo signals from all active receiving channels to generate a focused echo signal.

2. The imaging system of claim 1 wherein the full aperture and the array aperture at any step change are chosen so that a predetermined time error is not exceeded for echoes originating at all ranges up to the maximum range and received by active array elements.

3. The imaging system of claim 2 wherein the focal length of said transducer array assembly is 0.8 to 0.9 of the maximum range.

4. The imaging system of claim 3 wherein said row of transducer elements is curved symmetrically about the midpoint of the array.

5. The imaging system of claim 3 wherein said row of transducer elements is flat and said transducer array assembly further includes a converging acoustic lens made of a material in which the velocity of sound is faster than in water.

6. The imaging system of claim 3 wherein said aperture control means comprises a gain control in every receiving channel which has low and high values and further comprises means for adjusting said gain controls to initially select the high gain value for a central group of channels and thereafter select the high gain value for other pairs of channels, one at either side, to change the array aperture symmetrically by steps.

7. The imaging system of claim 6 wherein said means for adjusting the gain controls includes a range computer comprising a counter, a start pulse generator for initiating generation of said element excitation pulses and for clearing said counter, and a controller responsive to the counter outputs.

8. The imaging system of claim 7 further including means for compensating the overall gain of said focused echo signal so as to maintain uniformity of gain as the array aperture increases.

9. A sector scan ultrasonic imaging system comprising:
    a curved transducer array including a row of transducer elements at physical locations such that there are equal time delays for sound propagating from a focus to all elements of the array, the focal length of said curved array being about 0.8 to 0.9 times the maximum range, said array elements being selectively operable during alternate transmission and echo reception periods to generate angulated beams of ultrasound for scanning an object region and to generate received echo electrical signals,
    a plurality of transmitting channels for producing array element excitation pulses in time sequence, and a plurality of receiving channels for variably delaying the received echo signals to focus the echoes, aperture control means for increasing the number of active array elements and receiving channels as a function of range during each echo reception period by initially rendering active a central group of receiving channels and thereafter rendering active additional pairs of receiving channels to change the array aperture symmetrically by steps between the minimum range and a specified fraction of maximum range, the full aperture being maintained thereafter out to maximum range, and means for summing the delayed echo signals from all active receiving channels to generate a focused echo signal.

10. The imaging system of claim 9 wherein the specified fraction of maximum range is about one-half the maximum range.

11. The imaging system of claim 9 wherein said aperture control means comprises a gain control in individual receiving channels which has low and high values and further comprises means for adjusting said gain controls to high value in a sequence to increase the array aperture by steps without exceeding a predetermined time error at any range.

12. The imaging system of claim 11 wherein said means for adjusting said gain controls includes a counter which is fed pulses from an oscillator and incrementally increases the computed range, a start pulse generator for initiating generation of said element excitation pulses and for clearing said counter, and a controller for said gain controls which is responsive to the counter outputs and computed range.

* * * * *